United States Patent
Shao et al.

(10) Patent No.: US 9,492,123 B2
(45) Date of Patent: Nov. 15, 2016

(54) MOLECULAR IMAGING APPARATUS AND METHOD

(75) Inventors: Lingxiong Shao, Saratoga, CA (US); Douglas B. McKnight, Cleveland, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1393 days.

(21) Appl. No.: 12/302,929

(22) PCT Filed: May 24, 2007

(86) PCT No.: PCT/US2007/069599
§ 371 (c)(1),
(2), (4) Date: Dec. 1, 2008

(87) PCT Pub. No.: WO2007/143403
PCT Pub. Date: Dec. 13, 2007

(65) Prior Publication Data
US 2009/0237500 A1    Sep. 24, 2009

Related U.S. Application Data

(60) Provisional application No. 60/803,773, filed on Jun. 2, 2006, provisional application No. 60/820,965, filed on Aug. 1, 2006.

(51) Int. Cl.
*A61B 6/03* (2006.01)
*A61B 5/00* (2006.01)
*A61B 6/00* (2006.01)

(52) U.S. Cl.
CPC . *A61B 6/03* (2013.01); *A61B 6/00* (2013.01); *A61B 5/0013* (2013.01)

(58) Field of Classification Search
CPC ........................................................ A61B 6/03
USPC .............. 424/9.1, 9.3; 348/77; 600/409, 436
See application file for complete search history.

(56) References Cited

U.S. PATENT DOCUMENTS

| 6,679,844 B2 | 1/2004 | Loftman et al. |
| 7,433,507 B2 * | 10/2008 | Jabri ..................... G06T 11/005 |
| | | 382/128 |
| 2003/0036700 A1 | 2/2003 | Weinberg |
| 2003/0156684 A1 | 8/2003 | Fessler |

(Continued)

FOREIGN PATENT DOCUMENTS

| JP | 63200086 A | 8/1988 |
| WO | 2004057515 A2 | 7/2004 |

(Continued)

OTHER PUBLICATIONS

Liu, J., et al.; The Development of a New Version of Multifunctional Radioactive Nuclide Diagnostic Instrument; 2000; Chinese Journal of Medical Instrumentation; 24(3)143-146.

*Primary Examiner* — Aaron Strange

(57) ABSTRACT

A nuclear imaging chain (100) includes a molecular agent (102), an acquisition system (104), a reconstruction system (106), a detection system (108), and a display system (110). The various components of the imaging chain are optimized according to desired optimization criteria. The optimized characteristics of the imaging chain (100) may include one or more an agent characteristic, an acquisition characteristic (127), a reconstruction characteristic (143), a detection characteristic (159), and a display characteristic.

37 Claims, 9 Drawing Sheets

(56) References Cited

U.S. PATENT DOCUMENTS

| | | |
|---|---|---|
| 2004/0021081 A1 | 2/2004 | Rempel |
| 2005/0055178 A1 | 3/2005 | Phillips et al. |
| 2005/0097545 A1* | 5/2005 | Tarbox et al. ............... 717/176 |
| 2005/0149877 A1 | 7/2005 | Rice et al. |
| 2005/0187476 A1 | 8/2005 | Chomas et al. |

FOREIGN PATENT DOCUMENTS

| | | |
|---|---|---|
| WO | 2006054296 A2 | 5/2006 |
| WO | 2007034342 A2 | 3/2007 |

* cited by examiner

MOLECULAR IMAGING APPARATUS AND METHOD

CROSS REFERENCE TO RELATED APPLICATIONS

This application claims the benefit of U.S. provisional application Ser. No. 60/803,773 filed Jun. 2, 2006 and U.S. provisional application Ser. No. 60/820,965 filed Aug. 1, 2006, both of which are incorporated herein by reference.

The present application relates to molecular imaging in medicine. While it finds particular application to nuclear medicine imaging, it also relates to other imaging modalities in pre-clinical and other non-medical environments.

Nuclear medicine imaging, is a branch of medical diagnostic imaging which measures the distribution of a radiopharmaceutical in biological systems of a patient. Nuclear imaging is particularly useful for providing information in both functional level and molecular level, and is widely used in the diagnosis and treatment of cancer and heart disease, in medical and pharmaceutical research, and in other clinical and research applications.

In view of their wide range of clinical applications, general purpose nuclear imaging scanners have become widely available. Traditionally, these scanners have included gamma cameras such as single photon emission computed tomography (SPECT) scanners. More recently, positron devices such as positron emission tomography (PET) scanners have gained clinical acceptance. General purpose scanners are typically adapted or can be configured to image various parts of the body (cardiac and body scans being two common examples) and typically include various image acquisition, reconstruction, display, and other protocols that can be adjusted based on the requirements of a particular scan.

Examples of commercially available gamma cameras include the Skylight™, Forte™, Meridian™, and CardioMD™ scanners manufactured by Philips Medical Systems. An example of a well-known PET scanner is the Gemini™ system, available from Philips Medical Systems. Still other hybrid scanners, which include both a nuclear medicine scanner and an imaging modality such as computed tomography (CT) or magnetic resonance (MR) which provides anatomical or other complementary information, have also been developed. Example of hybrid scanners are the Gemini™ hybrid PET/CT system and Precedence™ hybrid SPECT/CT system, which are also available from Philips Medical Systems.

Nuclear medicine scanners are also well suited for use in the emerging field of molecular imaging (MI). Generally speaking, MI uses molecular agents to provide information about molecular pathways in the body, and especially those that are key targets in disease processes. MI has the potential to find, diagnose and treat disease in vivo (i.e., inside the body), as well as the ability to depict how well a particular treatment is working.

The development of MI has been aided by recent advances in molecular and cell biology techniques, new methods of combinatorial drug design, and high throughput testing. Examples of particularly promising MI techniques include radiolabeled antibody imaging, radioisotope lymphatic mapping, and radiolabeled receptor imaging.

Generally speaking, radiolabeled antibody imaging uses radiopharmaceuticals having antibodies or antibody fragments that are targeted to tumor surface protein antigens. Examples of radiolabeled antibody imaging agents include Indium-111 capromab pendetide (ProstaScint™, technetium Tc-99m arsitumomab (CEA-Scan™), and satumomab pendetide (Onco-Scint CR/OV™).

Radioisotope lymphatic mapping is dependent on the rate of transport and movement of a tracer through a lymphatic pathway, which is in turn dependent on the tracer particle size. The ideal lymphoscintigraphy agent should pass relatively quickly from the injection site to the lymphatic system, but be retained in the lymph nodes for a period of time which is consistent with an imaging procedure. While lymphatic mapping has been performed using radiopharmaceuticals such as technetium Tc 99m sulfur colloid, additional research is likely to yield additional and still more effective agents.

Radiolabeled receptor imaging is premised on the idea that different tumors may overexpress certain receptor types. Specific peptides that bind to these receptor types can be labeled with certain radioisotopes and imaged. Currently available agents include pentetreotide (OctreoScan), technetium Tc 99m depreotide (Neotect), and technetium Tc 99m apcitide (Acutect).

Of course, the above are but a few examples of existing radiotracers and their applications in nuclear imaging; future research is also likely to increase the range and applicability MI techniques both in nuclear imaging and in other modalities. Depending on the application needs and their chemistries, various other isotopes can be used for radiolabelling molecular agents, examples including, but not limited to, Tc-99m, In-111, Ga-68, I-123, I-131, Tl-201, Krm-81, Y-90, and Re-188.

While MI techniques and agents can be developed using general purpose nuclear (or other modality) scanners, there remains room for improvement. Typically, a pharmaceutical developer will develop an agent for a particular disease based on a desired specificity, dynamic performance, dose requirement, clearance, and like characteristics. The developer typically uses an available camera as an imaging device to validate the agent. In such a situation, the developer typically has limited ability to modify the imaging device to meet the specific requirements of the agent. For example, an agent may have a good biological correlation to disease but also have a fast clearance for which the camera system is not designed. If the agent binds well to a disease site but is also relatively non-specific, noise may be introduced. As yet another example, the agent may reach steady state relatively slowly so that the relative distribution of the activity changes with time. In each of these examples, identification or acceptance of an effective agent or application may be delayed. In extreme cases, an otherwise promising agent might even be missed entirely.

The interplay of agent and scanner characteristics can also affect the value of the scan data in clinical or research applications. For example, the protocols used in nuclear cameras have traditionally been based on a technology-based model in which the user or operator selects the desired acquisition, reconstruction, display, and other protocols on an individual basis. While such a model has proven successful in general purpose use, it can be sub-optimal in situations involving the use of various, specialized MI agents having their own unique requirements.

Aspects of the present invention address these matters, and others.

In accordance with one aspect, a functional imaging system includes an acquisition system, a reconstruction system, and a display system. The functional imaging system is selectively optimizable for use with a molecular agent. The functional imaging system further includes means for receiving an external input indicative of a desired molecular imaging agent, means for automatically adjusting at least one of an acquisition system characteristic, a reconstruction system characteristic, and a display system characteristic based on the desired molecular agent.

According to another aspect, a molecular imaging method includes receiving a user input indicative of a molecular imaging agent, acquiring molecular imaging scan data according to an acquisition protocol, reconstructing the scan data according to a reconstruction protocol, and displaying information indicative of the of the reconstructed scan data according to a display protocol. At least one of the acquisition protocol, the reconstruction protocol, and the display protocol are automatically established by a computer based on the user input.

According to another aspect of the invention, a method includes identifying pertinent characteristics of a molecular agent, identifying pertinent characteristics of an imaging system, evaluating the performance of an imaging chain, based on a result of the evaluation, adjusting a characteristic of at least one of the molecular agent and the imaging system, and providing at least one of a molecular agent and an imaging system which includes the adjusted characteristic.

According to another aspect, a computer readable storage medium contains a computer readable data structure for use in molecular imaging. The data structure includes at least a first imaging system identifier and at least a first imaging system characteristic associated with the at least a first imaging system identifier. The at least a first imaging system characteristic identifies a desired configuration of the first imaging system in a molecular imaging procedure using a specified molecular agent.

According to still another aspect of the invention, a molecular imaging method includes using a communication network to access a remotely located data structure, downloading information indicative of a desired imaging system characteristic from the data structure, where the desired imaging system characteristic is associated with a specified molecular agent. The method also includes using the downloaded data to establish a characteristic of an imaging system and operating the imaging system according to the established characteristic.

According to another aspect, a computer readable storage medium contains instructions which, when executed by a computer, cause the computer to carry out a method which includes receiving an input indicative of a desired molecular agent, identifying, based on the desired molecular agent, at least a first imaging system characteristic, and communicating the imaging system characteristic to the imaging system.

According to another aspect, a user interface apparatus includes a computer input device which receives a user input which identifies one of at least first and second molecular agents and a computer display device which displays information derived from an imaging examination of an object conducted using the identified molecular agent. The information is displayed in human readable form according a display protocol which is automatically established based on the user input.

According to another aspect, a method of providing an imaging agent includes defining a region of interest and an imaging modality, selecting a molecular imaging agent which targets the region of interest and which is visible in the defined modality, defining a set of parameters that allow for an optimization of an imaging system of the defined modality, and providing the set of parameters to the imaging system.

Still further aspects of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIGS. 1A-D depict a nuclear medicine imaging chain.

Figure 1A:
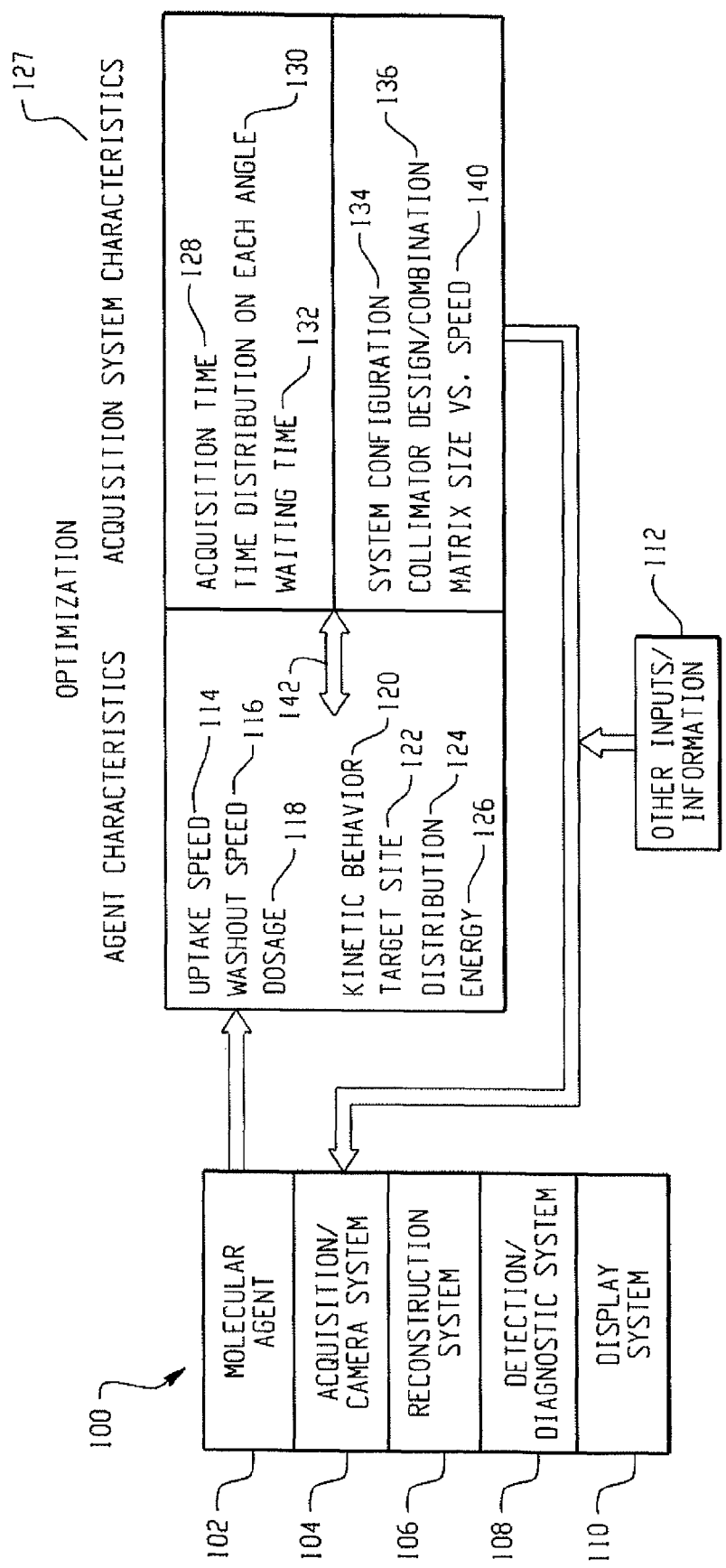

Viewed from a first perspective, it is desirable to provide a solution-based system in which the molecular agent 102 is considered as a system design component together with mechanical, electrical, and software, and other components of an integrated molecular agent—imaging system. Viewed from yet another perspective, it is also desirable to provide an improved workflow in which the various components of the molecular agent—imaging system are presented to the user in an integrated fashion.

The interplay between various parts of a nuclear imaging system in which a molecular agent 102 is modeled as part of an imaging chain 100 is depicted in FIGS. 1A-1D. The imaging chain 100 includes the molecular agent 102, an acquisition/camera system 104, a reconstruction system 106, a diagnostic system 108, a display system 110, and other inputs 112.

The molecular agent 102 has characteristics such as uptake speed 114, washout speed 116, dosage 118, kinetic behavior 120, a target site 122, distribution 124, and energy 126, which influence its behavior and effectiveness an imaging agent. The molecular agent 102 may also include a therapeutic component.

With particular reference to FIG. 1A, the acquisition/camera system 104 includes a nuclear imaging system such as a SPECT or PET scanner which generates data indicative of radionuclide decays in a human patient or other object under examination. The acquisition system 104 typically includes various protocols or configuration options such as acquisition time 128, time distribution on each angle 130, waiting time 132, system hardware and/or software configuration 134, collimator system configuration 136, and matrix size 140.

As shown by the double arrows 142, one or more of the molecular agent 102 characteristics have the potential to influence the desired acquisition system characteristics 127. Consequently, it is desirable to optimize the various parameters so that the imaging chain 100 operates in an integrated fashion.

Generally speaking, shorter acquisition times 128 are preferred. Where the kinetic behavior 120 of the agent 102 is of interest, however, it may be desirable to perform a series of shorter acquisitions. In addition, it is generally desirable to minimize the agent dose 118. The optimal dose 118 and acquisition time 128 are typically interrelated, taking into account factors such as uptake speed 114, patient tolerance, and image quality.

Particularly in SPECT imaging or other situations in which the scanner detector positions can be varied, it may also be desirable to vary the acquisition time as a function of angle as depicted at 130 so as to increase the statistics or otherwise optimize the data for subsequent reconstruction. For example, in the case of cardiac perfusion imaging, a front 180 degree acquisition is often used instead of spending half the acquisition time at the front 180 degree position and the other half at the rear 180 degree position. As is well known to those skilled in the art, such an arrangement trades resolution and uniformity for increased counts in the myocardium region.

Waiting time 132 following the introduction of the agent 102 is another relevant acquisition parameter. In many cases, the acquisition is started when the agent 102 is at or near the steady state. In other cases, and especially where the agent has a relatively longer uptake time, the desired wait time 132 may become a tradeoff between the steady state condition and the activity remaining in the body. By modeling the behavior of the agent during reconstruction, however, post-injection waiting time can often be reduced, and additional counts may also be obtained. To facilitate introduction of the agent 102, a desired agent injection or introduction protocol may also be established. The protocol is then communicated to an injector or other dose application device via a suitable interface for automatic or user-initiated introduction in coordination with the acquisition.

Acquisition system configuration 134 parameters may include both hardware and software parameters. Exemplary hardware configuration parameters include camera positioning parameters such as the angular or other physical relationship between the detectors (e.g. opposed, orthogonal, or other desired angular or physical relationship), detector radial position, and desired scan orbits (e.g., circular, elliptical, helical, or the like). Where the configuration of the acquisition system 104 can be adjusted, the adjustment may be performed as needed based on the requirements of a particular scan. Dedicated scanners which are optimized for use with a particular region of the anatomy (e.g., cardiac, breast, or brain systems) or pharmaceutical 102 characteristic (e.g., energy, count rate, or the like) are also contemplated. In the case of software or firmware, various configurations or modules may be provided.

The collimator system configuration 136 is typically selected to optimize the spatial resolution and sensitivity of the sampling, with the collimator or collimators used in a scan selected accordingly. In an exemplary case in which the region of interest is relatively small, a high resolution collimator (e.g. a fan or cone collimator) may be used to image a region of particular interest and a high sensitivity, lower resolution collimator may be used to obtain data from other portions of the object or patient. As still another example, a segmented collimator may be used. Yet another example includes the use of variable or adjustable collimators which allow the resolution, field of view, magnification/minification, or other characteristics of a particular collimator to be mechanically or otherwise adjusted.

Still another consideration is matrix size 140, which is advantageously selected to optimize the relationship between processing time and image resolution. In clinical and other situations where speed is a key consideration, decreasing the processing time may be particularly desirable, especially as three dimensional (3D) reconstruction techniques become increasingly popular. Generally speaking, speed may also be increased by using a relatively more powerful or faster reconstruction computer(s), faster or more efficient reconstruction algorithms, or the like.

Figure 1B:
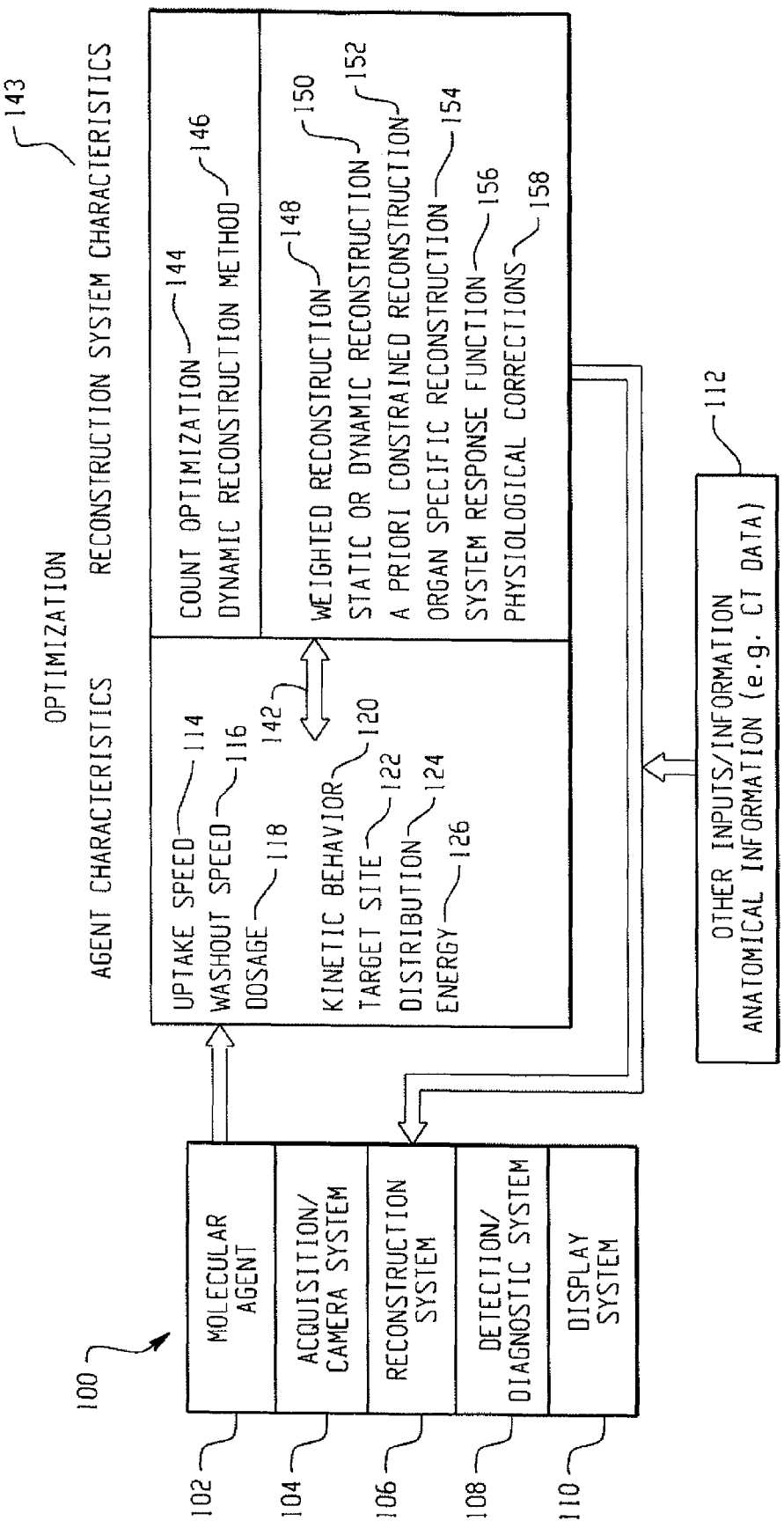

Turning now to FIG. 1B, the reconstruction system 106 reconstructs event data from the acquisition system 104 to generate volumetric data indicative of the radionuclide distribution in the patient or other object under examination. Various reconstruction techniques, including iterative and analytical techniques, are well known to those skilled in the art and may be selected based on application specific requirements. The reconstruction system 106 may include various characteristics 143 such as reconstruction protocols or configuration options, including count optimization 144, dynamic reconstruction 146, weighted reconstruction 148, static or dynamic reconstruction 150, a priori constrained reconstruction 152, organ specific reconstruction 154, a system response function 156, and physiological corrections 158.

A persistent issue in nuclear medicine imaging is the availability of counts. As a result, image quality may vary from patient to patient or between multiple scans of the same patient. Consequently, count optimization techniques 144 may be used to provide a more even image quality of a relatively wide range of count statistics. One suitable technique uses the dual match filter described in commonly owned U.S. Patent Application Ser. No. 60/720,431 filed Sep. 26, 2005, entitled Iterative Reconstruction with Enhanced Noise Control Fitter, which application is expressly incorporated by reference herein in its entirety.

Where the molecular agent 102 concentration is not at steady state during a scan, the data dynamically changes in the course of the acquisition. This is a particular issue in SPECT or other applications in which the detector projection angle changes with time. To reduce these effects, a dynamic reconstruction method 146 is used to account for the varying count rate.

Weighted reconstruction techniques 148 may also be used to preferentially weight desired portions of the projection data and hence reduce noise. For example, the projections acquired at certain angular projections may include more useful information. These projections may be preferentially weighted.

A priori constrained reconstruction techniques 152 anatomic or other known information to build boundary constraints during reconstruction. Where the location of the region interest is known, organ specific reconstruction techniques 154 may be used to minimize noise from other portions of the body.

The overall system response function 156 may vary for different agents 102, especially due to factors such as the isotope energy characteristics 126, collimator configuration 136, detector resolution, location of the object, and system configuration 134. In order to improve the image quality, a system response dependent resolution recovery method is usually used. Attenuation and scatter correction may be applied as appropriate.

Physiological corrections 158 may also be applied. Examples include respiratory and cardiac gated corrections and non-rigid image registration techniques. Still another involves the use of anatomical landmarks to help identify a region of interest. This can be particularly important in MI, as disease specific agents typically provide limited if any anatomical information. Typically, however, some key organs such as the heart, liver, and kidneys may be visible in the volumetric data. In addition to helping to locate a region of interest, the information can be used to reduce noise caused by activity in the organ. The detection/diagnostic system 108 may include functions such as quantification 160, kinetic parameters 162, object based segmentation, 164, object based post processing 166, object based search 168, and normal/abnormal index information 170.

Figure 1C:
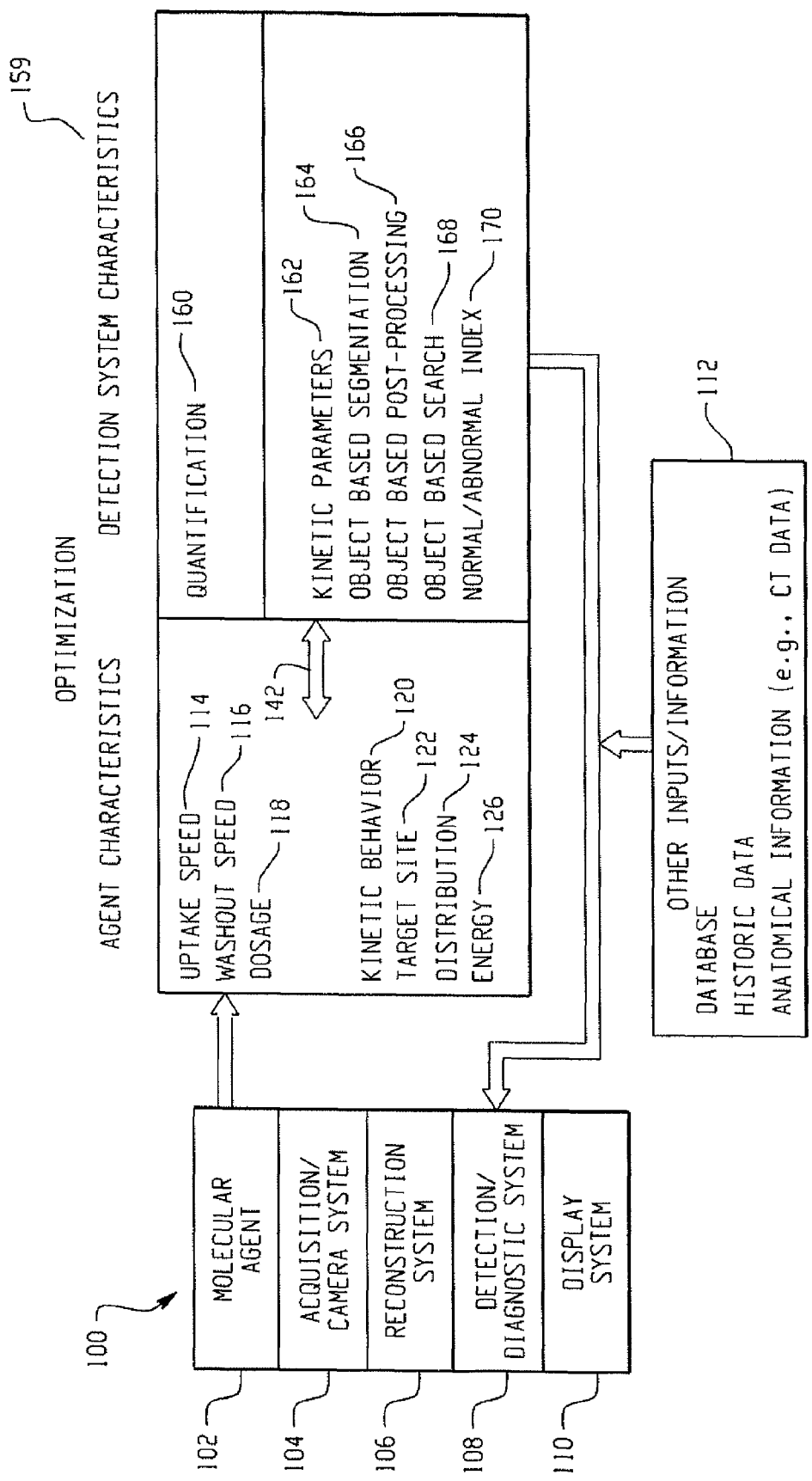

Turning now to FIG. 1C, the detection/diagnostic system 108 may include diagnostic index, computer assisted detection (CAD), computer assisted diagnostics (CADx), treatment planning or other functionalities which help the physician or other user to interpret the results of a scan or to plan a course of treatment. Typical detection/diagnostic system characteristics 159 include diagnostic protocols or configuration options such quantification information 160, kinetic parameters 162, object based segmentation 164, object based post processing 166, object based search 168, normal/abnormal index 170, and treatment planning 171.

Traditionally, nuclear imaging techniques have provided some sort of qualitative information in certain imaging protocols. The usefulness of the scan data for a particular patient, and the uniformity of diagnostic results from scan-to-scan, patient-to-patient, and physician-to-physician can in many cases be improved by providing quantitative data 160 indicative of a parameter of interest. As will be appreciated, the parameter of interest, as well as the nature and presentation of the quantitative data, are strongly related to the particular molecular agent 102, the region of interest of the scan, and the like.

In certain situations, single image (steady state) information may provide only limited information relevant to a diagnosis or treatment. Consequently, kinetic parameters 162 may also be provided. Typically, the agent uptake process at the region of interest can be described by mathematical models (i.e., physiological modeling for the uptake). Commonly used models include first order, second order or third order compartmental models. Using a series of dynamic images, together with the injection characteristics, the relevant kinetic parameters 162 can be derived and presented in an appropriate way.

One or more of an object-based segmentation 164, post-processing 166, and search 168 may also be provided or otherwise optimized in connection with a given molecular agent 102. Segmentation 164 typically uses anatomical information (e.g., CT scan data) to segment or separate a region of interest from the surrounding anatomy. The segmented data can be used to improve reconstruction and post-processing. Object based post-processing 166 typically uses landmark information, segmented region information and the like to provide more specific post-processing and corrections. Search functions 168 typically use physiological and other information to identify relevant regions or areas of interest for presentation to the user.

Information from a scan may also be provided to a radiation therapy planning (RTP) or other treatment planning system. In one such implementation, the scan output is formatted or otherwise processed to conform to the requirements of the treatment planning system. A physician or other user may then notified that the scan results are available for conducting a treatment plan, for example by notifying the interested user or a hospital HIS/RIS system that the scan has been completed. The scan data itself may also be transmitted. In another implementation, some or all of the treatment planning functionality may be incorporated in the scanner, and the treatment planning initiated on an automatic or semi-automatic basis.

To further aid in the detection or diagnosis, normal/abnormal index information 170 such as CAD or CADx functionality may also be provided. Again, the precise functionality depends on the particular molecular agent 102 and other application specific requirements.

Figure 1D:
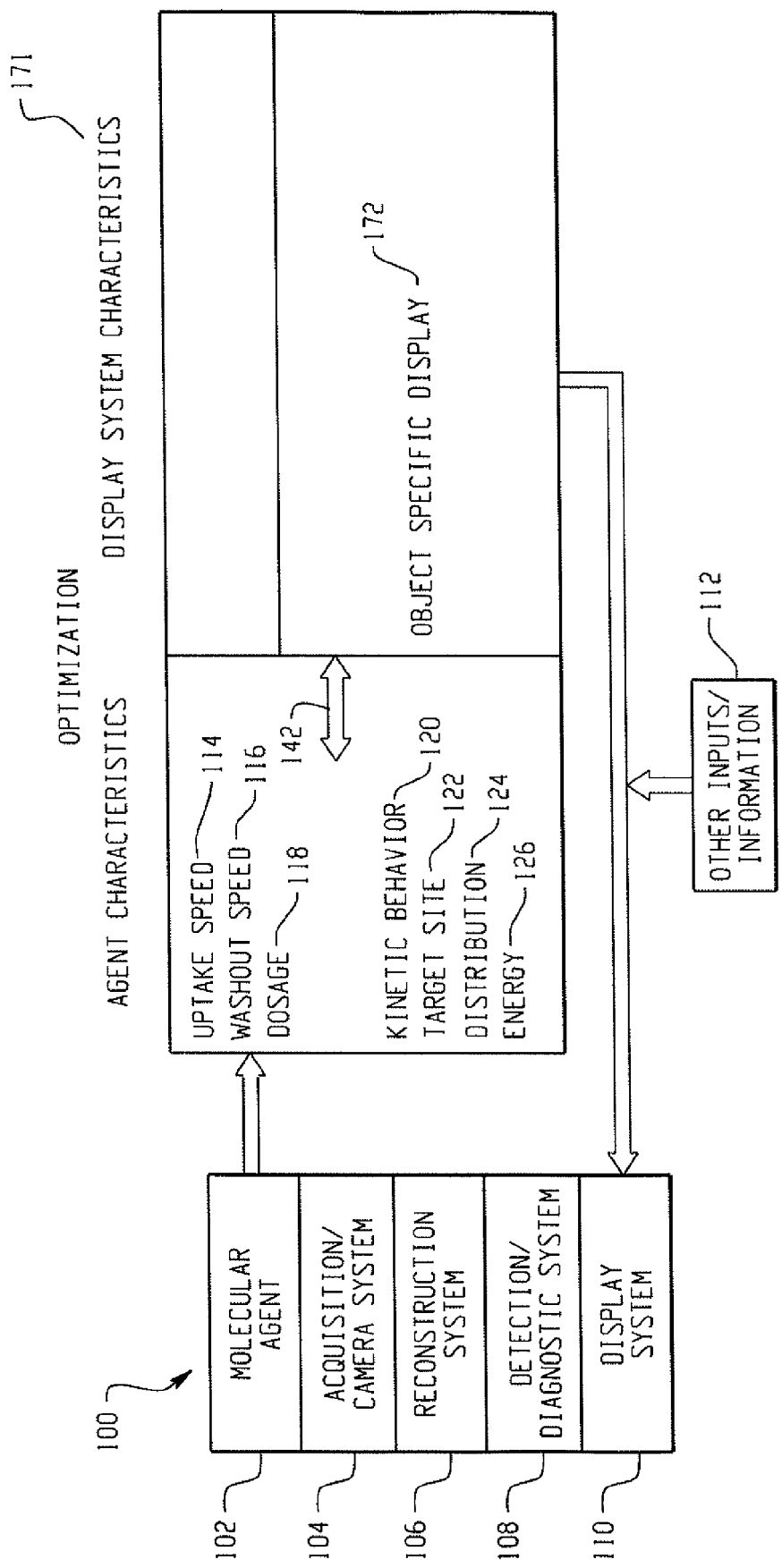

Turning now to FIG. 1D, the display system 110 typically presents the imaging information in human readable form on a monitor or display, films, printouts, or the like according to a desired set of display system protocols or configuration options 171. As will be appreciated, the information which is presented, as well as the form in which it is presented, varies as a function of the molecular agent 102, the region of interest, disease status, and other application specific requirements. The display system 110 is preferably optimized for use with the particular molecular agent 102 and/or application, the objective being that the relevant information is presented in a tracer and/or object specific display format 172 with a minimum of user intervention. For example, the image data may be presented as one or more image slices, three dimensional rendered views of a segmented region of interest, functional parameter maps, diagnostic annotations, and the like. Additional functionality such as is typically provided in connection with general purpose imaging packages may also be provided so that the user can further manipulate the image if so desired.

Figure 2:
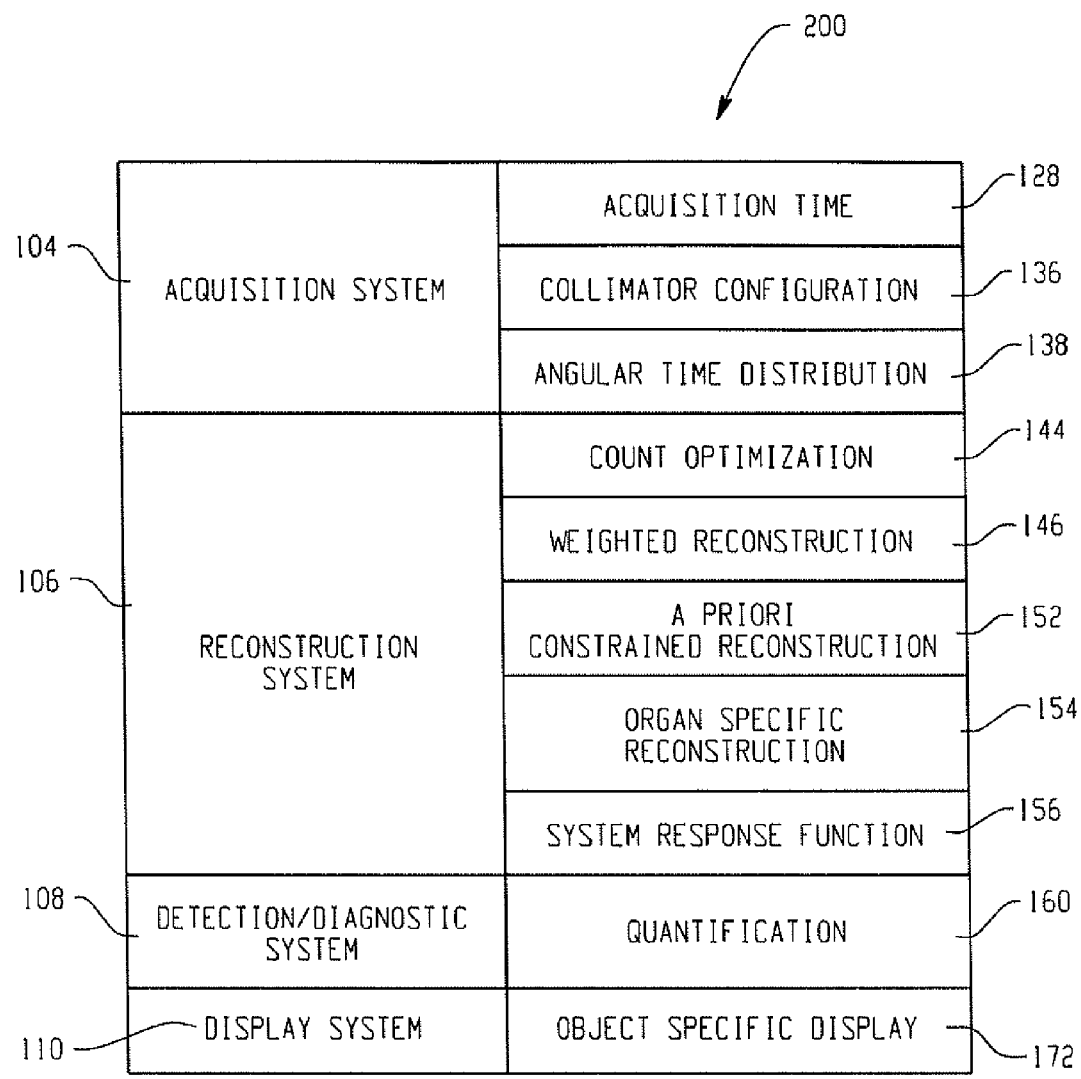
FIG. 2 depicts optimizations for an exemplary molecular agent.

Turning now to FIG. 2, optimizations for a general purpose SPECT system 200 in connection with an exemplary molecular agent such as indium In-111 capromab pendetide (ProstaScint) will now be described in one embodiment. As will be appreciated, Prostascint is a radiolabeled antibody imaging agent which is particularly well suited to imaging of the prostate in oncology applications.

In view of Prostascint's relatively long half-life and the relatively low uptake in the prostate area, dose becomes an important factor, resulting in relatively long imaging times. Therefore, it is desirable to decrease the acquisition time 128 while minimizing the impact on image quality. As Prostascint is known to be site specific, the angular time distribution 130 can be adjusted based on anatomical considerations. Because the prostate is a relatively small and defined region of the body, collimators 136 which provide relatively high spatial resolution in the region of the prostate may also be used. In order to increase the available counts, a collimator which provides a relatively lower spatial resolution in surrounding regions may be used.

Turning now to reconstruction parameters, Prostascint has a relatively low count rate and is thus a particular candidate for the use of count optimization techniques 144 such as dual match filtering. Angularly weighted reconstruction 148 may be applied, for example by preferentially weighting projections acquired from the front and rear of the patient relative those acquired laterally. Also in view of the relatively well defined region of the prostate, Prostascint imaging is a good candidate for one or more of a priori constrained 152 or organ specific 154 reconstruction, and also for optimization of the system response function 156.

Turning now to the detection system 108, Prostascint imaging is well suited to quantification 160. Similarly, the display system 110 may be optimized for presenting images relevant to the region of the prostate.

Though the foregoing example focused on Prostascint, optimizations specific to other agents or classes of agents (including but not limited to those noted above) and to other regions of interest may also be provided. Note also that the present techniques may also be applied to dual or multiple isotope imaging.

As will be appreciated from the foregoing discussion, obtaining the optimum or otherwise desired results with a given molecular agent 102 involves numerous protocols and other parameters which can affect the performance of the imaging chain 100. Selecting the various protocols can be difficult, time consuming, and error prone, particularly in clinical and research applications where the user's focus is on the results of an examination rather than the technical details of its implementation. Accordingly, in one implementation, some or all of the protocols or characteristics relevant to a particular molecular agent 102 are incorporated into the design of the imaging system in order to provide a dedicated system which is designed to operate with a particular agent or class of agents.

Figure 3:
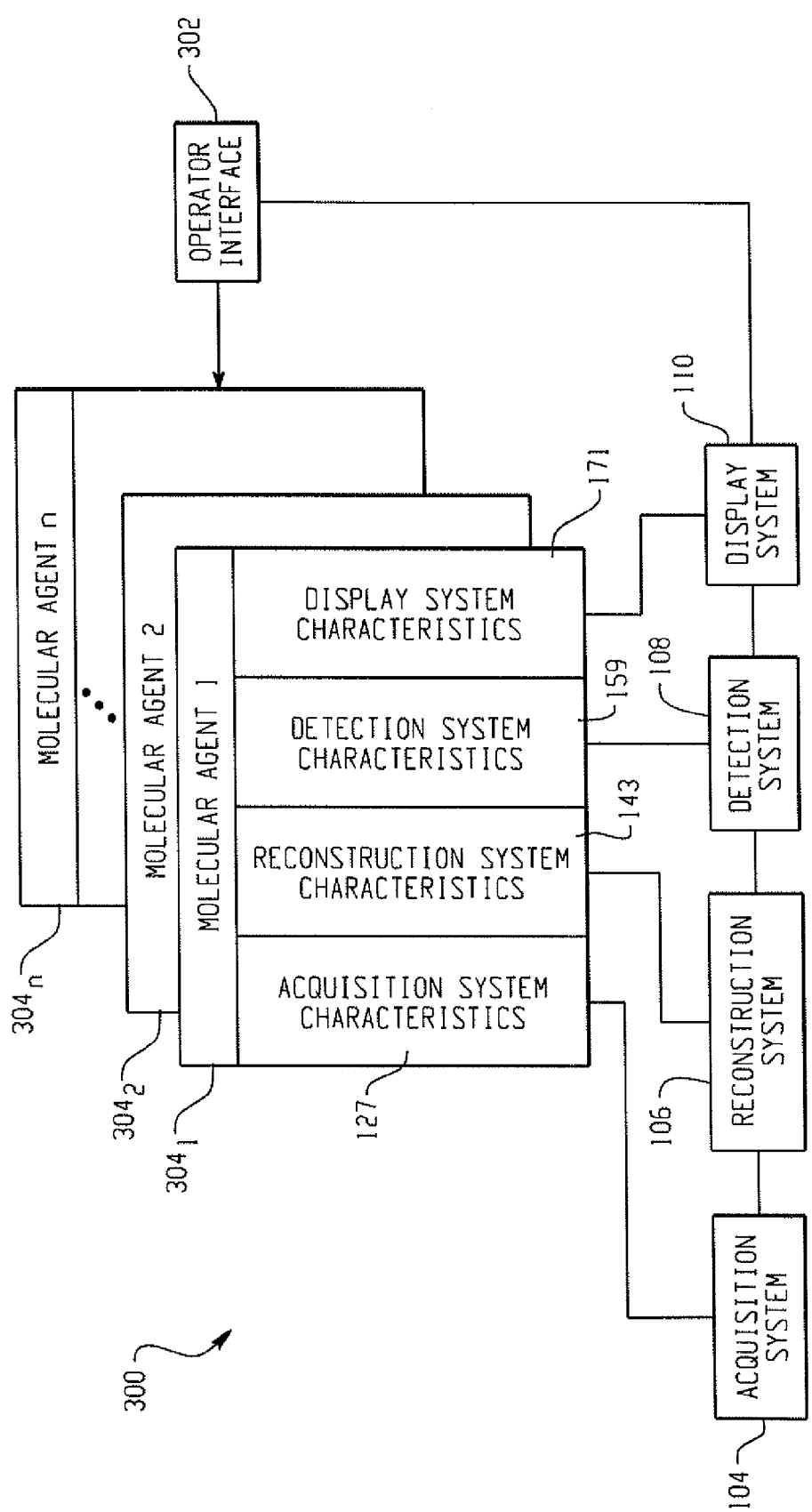
FIG. 3 depicts a nuclear medicine imaging system.

In other situations, it may be desirable to provide a general purpose or dedicated nuclear imaging system to which molecular agent 102 specific optimizations may be readily applied by a user based on the requirements of a given scan. With reference to FIG. 3, such an imaging system 300 includes an operator interface 302 which typically includes a computer or computer workstation having a monitor or other display and input devices such as a keyboard and mouse. The computer contains a processor which executes instructions stored on a computer readable storage medium (e.g., in a volatile or non-volatile memory contained in the computer or accessed over a suitable network) so as to carry out the desired functions. Direct interaction with a human user is advantageously provided via a graphical user interface (GUI).

The user interface 302 may also include other input and output devices which facilitate the transfer of data in a user-desired fashion, whether manually, semi-automatically, automatically, or otherwise. Non-limiting examples include optical (e.g., bar code or snowball), magnetic (e.g., magnetic card readers), radio frequency (e.g., radio frequency identification (RFID) or near field communication (NFC)), audio or other scanners or readers. Still other interfaces include network or other communications interfaces such as hospital information system/radiology information system (HIS/RIS), digital communications in medicine (DICOM), local area network (LAN), wide area network (WAN), internet, and wired or wireless communications devices. As will be appreciated, such interfaces typically allow the user to set the desired scan protocols, initiate and terminate scans, view and/or manipulate the resultant scan data, and otherwise inter act with or transfer desired data to and/or from the scanner.

When configured as a general purpose imaging system, the operator interface 302 preferably allows the user to operate the system as a conventional scanner, for example using conventional radiopharmaceuticals or to image desired regions of interest. The operator interface also allows the user to identify an imaging agent 304 to be used in a particular scan.

One or more of desired acquisition system 127, reconstruction 143, detection system 159, and display system 171 characteristics for one or more molecular agents $304_1$, $304_2$ . . . $304_n$ are stored in a computer readable memory associated with the imaging system 302. When a particular molecular agent 304 is selected by the operator through the operator interface 302, the relevant characteristics are automatically established for the various parts of the imaging system. In one implementation, the various protocols are automatically established without user intervention, and processing may proceed automatically from one sub-system to the next. In another implementation, the user may be given the opportunity to view or modify one or more of the protocols. Where collimator 136 or other configurations must be performed by the user, the user is also instructed to configure the system as required. If the imaging system 302 includes or otherwise interfaces with an injector, a desired injection protocol may also be automatically established based on the selected agent.

The various characteristics may be stored and selected in various ways. In one implementation, the characteristics are stored in a database which is accessed based on the selected molecular agent 304. In one implementation, the database is stored in the imaging system 300 disk or other memory. In other, the database may be stored remotely from the imaging system and accessed through a local area network (LAN), a wide area network (WAN), a hospital information system/radiology information system (HIS/RIS), the internet, or other suitable communications network. In another, the operator interface 302 includes one or more molecular imaging application software packages contained in a computer readable memory and which are directed to a particular agent or class of such agents. The user selects the application software package which is relevant to a particular scan.

Figure 4:
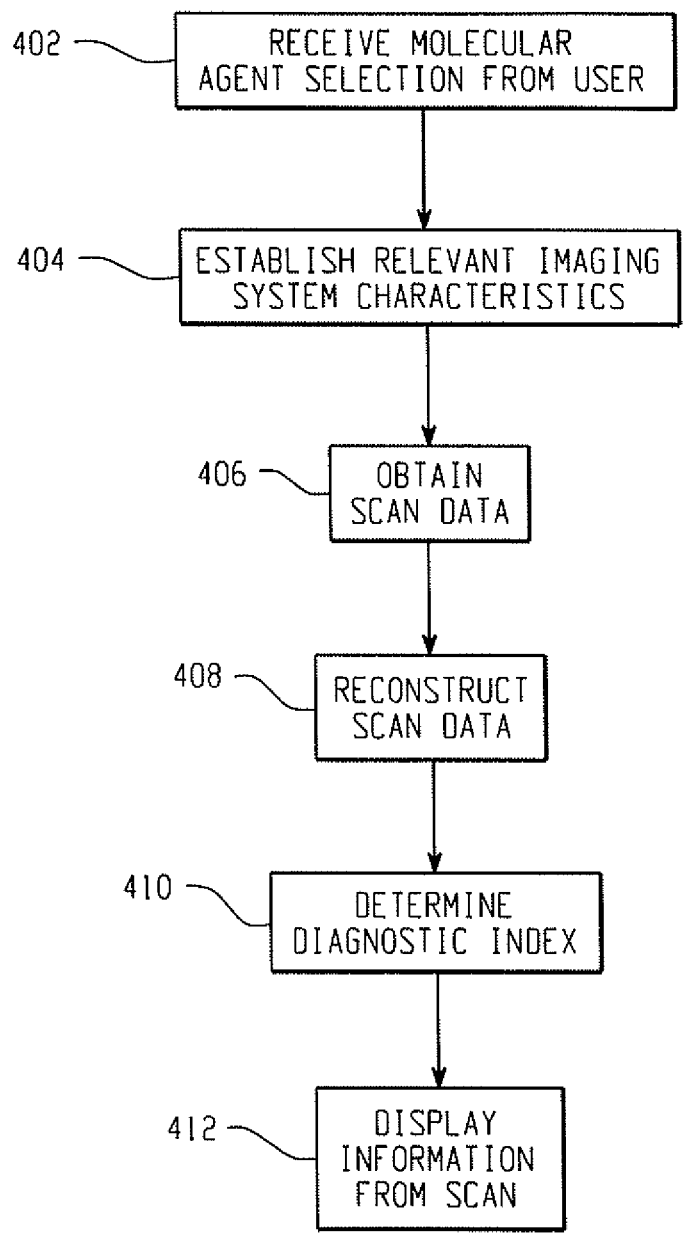
FIG. 4 depicts a molecular imaging method.
Figure 6:
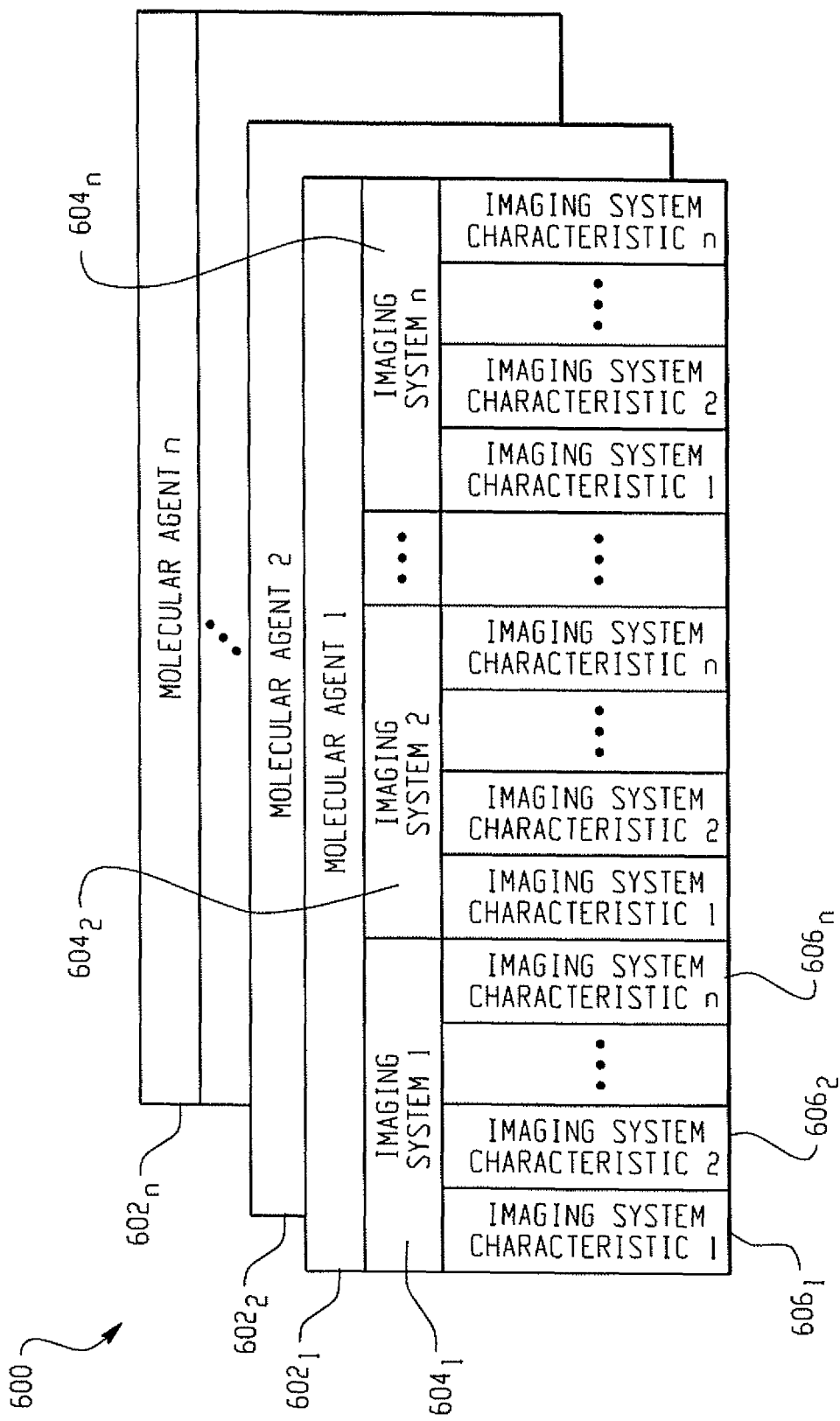
FIG. 6 depicts a computer database containing imaging system characteristics for a plurality of imaging systems.

With reference to FIG. 6, desired imaging system characteristic(s) $606_1$, $606_2$ . . . $606_n$ for each of a plurality of imaging systems $604_1$, $604_2$ . . . $604_n$, and for one or more molecular agents $602_1$, $602_2$ . . . $602_n$ are stored in a computer readable database. The imaging systems 604 may be imaging systems provided by different imaging system vendors, different models or versions of imaging systems 604 provided by a given vendor, or a combination of both. The imaging system characteristics 606 may be different for each system model and/or vendor. The database, which is particularly well suited for remote implementation, is accessed from time to time as needed to download the desired information. In operation, and with reference to FIG. 4, the molecular agent selection is received from the user at step 402. As noted above, the user may select the agent in various ways, for example by selecting the desired agent from a list of such agents, by selecting one or more application software packages pre-configured for an agent or class of agents, or by entering or selecting patient demographic information which is then associated with an agent and/or imaging protocol prescribed by the patient's physician.

In one typical workflow, the user or operator may be presented with a patient (or series of patients) who have already been prescribed to receive a particular imaging agent and/or a desired scan protocol (e.g., a cardiac, whole body, or other scan). In one example implementation, pertinent patient demographic, agent, and/or protocol information is carried on a traveler which accompanies a particular patient. In such a situation, the user input may be provided by scanning the traveler (automatically without direct user intervention or otherwise) to retrieve the desired information. In another example, the user input may be provided by manually entering patient demographic information, selecting a particular patient from a list of patients to be scanned, or received via a suitable scanner or reader (automatically or otherwise). The demographic information may then be matched with corresponding molecular agent, scan, and/or other protocol information received from a HIS/RIS system or other external database. Note also that the user may also be afforded to populate some or all of the database or the select some or all of the characteristics of the application software based on the user preferences or requirements.

At step 404, the relevant imaging system characteristics and protocols are automatically established based on the agent selected by the user. As noted above, the user may also be instructed to configure collimator 136 or other settings as needed.

At step 406, the acquisition system 104 is used to obtain the scan data according to the identified acquisition protocol.

At step 408, the reconstruction system 106 reconstructs the scan data according to the identified acquisition protocol.

At step 410, the detection system 108 provides the desired diagnostic information according to the desired diagnostic information protocol.

At step 412, the display system 110 generates the desired human readable output information based on the desired display protocol.

Note that the various characteristics and protocols do not need to be established prior to the scan. Thus, for example, they may be provided to relevant system components as they are executed or otherwise activated during the imaging process. Addition or different system components and characteristics may also be provided.

Figure 5:
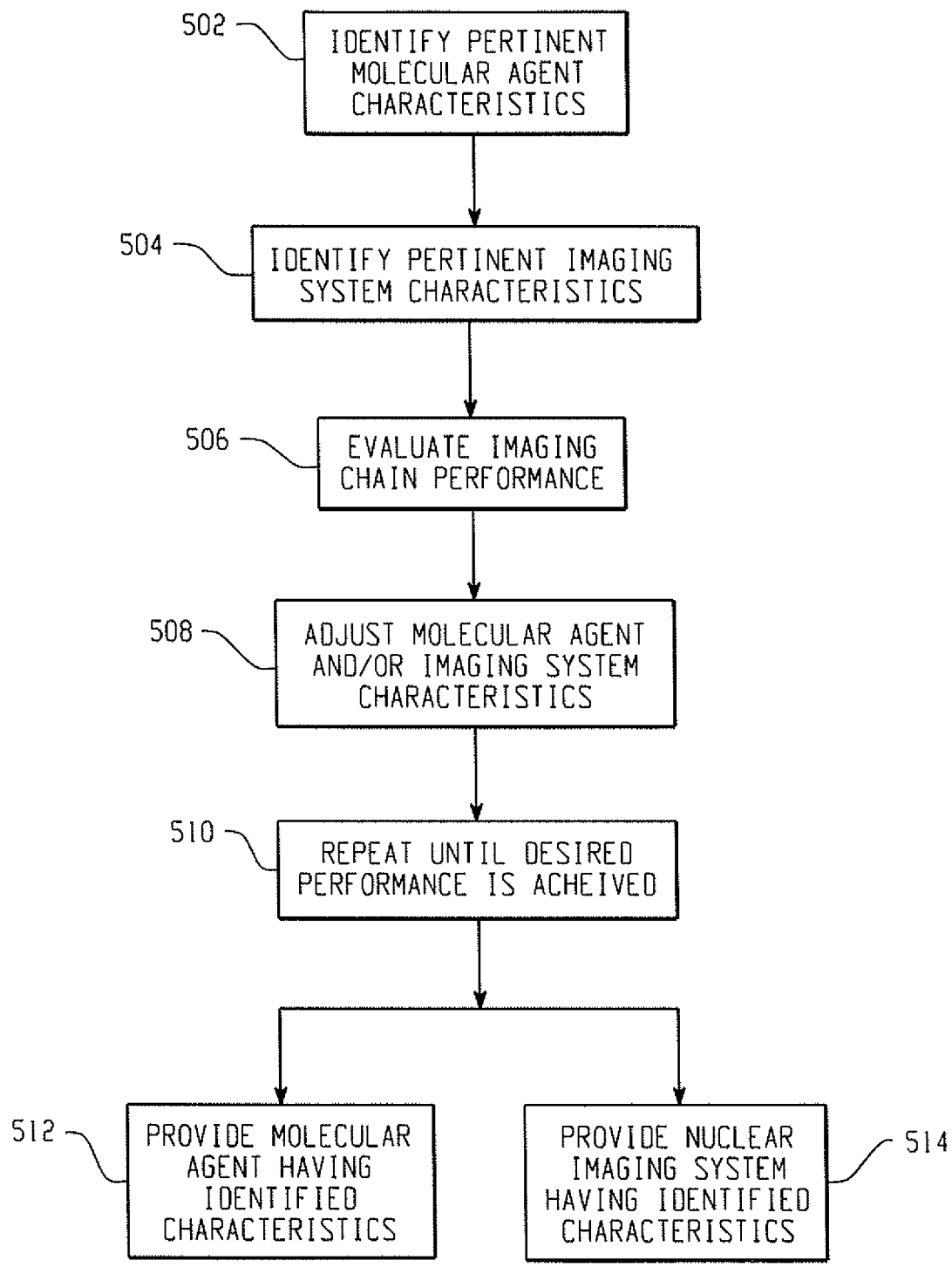
FIG. 5 depicts a method for designing a molecular imaging chain.

Turning now to FIG. 5, a method of optimizing a molecular imaging chain is described.

At step 502, the pertinent molecular agent characteristics are identified.

At step 504, the pertinent imaging system characteristics are identified.

At step 506, the performance of the imaging chain is evaluated for a selected set of characteristics, for example by way of one more simulations or test scans.

At step 508, the characteristics of the molecular agent and/or the imaging system are adjusted.

As shown at step 510, the steps of evaluating and adjusting are repeated until a desired performance is obtained, in which case the desired molecular agent and imaging system characteristics are identified.

At step 512, a molecular imaging agent having the identified characteristics may be provided. Note also that a family of related agents, each optimized to provide a desired imaging chain characteristic, may also be provided.

At step 514, a nuclear imaging system having the identified characteristics may be provided. As noted above, the optimized nuclear imaging system may be provided in various ways. For example, a dedicated nuclear imaging system may be provided, a general purpose imaging system may be provided with a database or other information indicative of the characteristics for a selected molecular agent, or the imaging may be provided with one or more software application packages which operate in conjunction with the imaging system.

As noted above, a particular advantage of such a technique is that the performance of the imaging chain may be evaluated in an integrated manner, and the various components of the imaging chain designed accordingly. Compared to conventional techniques in which the molecular agent and imaging system characteristics are developed separately, more effective results may be obtained.

While the foregoing discussion has focused primarily on nuclear imaging, it is also applicable to magnetic resonance (MR), computed tomography (CT), ultrasound (US) and other modalities which can be used in connection with suitable molecular agents and markers. While the specific implementation of the molecular agent and the imaging system varies based on the modality, it nonetheless remains desirable to optimize the various components of the molecular agent-imaging system. In MR, for example, it may be desirable to optimize one or more characteristics such as of the applied pulse sequence, the gradient coils, the radio frequency (RF) transmit and receive coils, the reconstruction parameters. In CT, for example, it may be desirable to desirable to optimize one or more of the x-ray voltage, the applied dose, scanning trajectory, collimation, gating techniques, or other parameters. Of course, still other protocol and parameter optimizations will be recognized by those skilled in the art based on application and modality specific requirements.

Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A functional imaging system comprising an acquisition system, a reconstruction system, and a display system, wherein the functional imaging system is selectively optimizable for use with a molecular agent, and wherein the molecular imaging system further includes:
   an interface that receives an external input indicative of a desired molecular imaging agent;
   a processor that automatically adjusts at least a reconstruction parameter of the reconstruction system wherein the reconstruction system employs the reconstruction parameter to reconstruct an image based on the desired molecular agent wherein the reconstruction parameter includes count optimization through a dual match filter.

2. The functional imaging system of claim 1 further including a disease detection system and wherein the processor automatically adjusts at least one of an acquisition system characteristic, a display system characteristic or a disease detection system characteristic of the disease detection system.

3. The functional imaging system of claim 2 wherein the disease detection system characteristic includes at least one of a quantification information, a kinetic parameter, an object-based segmentation, a normal/abnormal index, and a treatment plan.

4. The functional imaging system of claim 2 wherein the processor adjusts an acquisition protocol.

5. The functional imaging system of claim 2 wherein the processor adjusts a display protocol.

6. The functional imaging system of claim 1 wherein the functional imaging system is a general purpose nuclear imaging system.

7. The functional imaging system of claim 1 wherein the processor communicates with a database which includes an imaging system characteristic for at least a first molecular agent.

8. The functional imaging system of claim 1 wherein the reconstruction parameter includes one of a reconstruction protocol, a reconstruction algorithm, or a reconstruction system response function.

9. The functional imaging system of claim 1 wherein the processor processes an application software package which is selected by the user based on the desired molecular imaging agent.

10. The functional imaging system of claim 1 wherein the molecular imaging agent includes at least one of a radiolabeled antibody agent, a lymphoscintigraphy agent, and a radiolabeled receptor agent.

11. The functional imaging system of claim 10 wherein the agent includes indium.

12. A molecular imaging method comprising:
   receiving a user input indicative of a molecular imaging agent;
   acquiring molecular imaging scan data according to an acquisition protocol;
   adjusting, automatically and with a processor, a reconstruction protocol employed by a reconstruction system to reconstruct an image wherein an adjustment to the reconstruction protocol includes adjusting count optimization through a dual match filter;
   reconstructing the scan data according to the reconstruction protocol; and
   displaying information indicative of the of the reconstructed scan data according to a display protocol;

wherein the reconstruction protocol is automatically established by a computer based on the user input.

13. The method of claim 12 wherein the acquisition protocol, the reconstruction protocol, and the display protocol are automatically established by a computer.

14. The method of claim 13 including requesting a user to confirm the established protocol.

15. The method of claim 13 wherein the molecular imaging agent includes indium.

16. The method of claim 12 including retrieving information indicative of a desired protocol from a database.

17. The method of claim 12 wherein the user input includes patient demographic information and the method includes associating the patient demographic information with a molecular imaging agent.

18. The method of claim 12 wherein the acquisition protocol is automatically established by a computer based on the molecular imaging agent selection and wherein the acquisition protocol includes an acquisition time.

19. The method of claim 12 wherein the molecular imaging scan data is nuclear imaging scan data, the reconstruction protocol is automatically established by a computer based on the molecular imaging agent selection and wherein the reconstruction protocol includes a count optimization.

20. The method of claim 12 wherein the display protocol is automatically established by a computer based on the molecular imaging agent selection and wherein the display protocol includes an organ specific display setting.

21. The method of claim 12 wherein the molecular imaging agent is an oncologic agent.

22. The method of claim 12 wherein the molecular imaging agent is targeted to the prostate.

23. A molecular imaging method comprising:
using a communication network to access a remotely located data structure;
downloading information indicative of a desired imaging reconstruction system parameter from the data structure, wherein the desired imaging reconstruction system parameter is associated with a specified molecular agent, includes count optimization through a dual match filter, and is employed by a reconstruction system to reconstruct an image;
using the downloaded data to establish a reconstruction parameter of an imaging system; and
operating the imaging system according to the established reconstruction parameter.

24. The method of claim 23 including specifying an imaging system type and downloading information specific to the specified imaging system type.

25. The method of claim 23 includes identifying a patient and downloading information specific to the identified patient.

26. A non-transitory computer readable storage medium containing instructions which, when executed by a computer, cause the computer to carry out a method comprising the steps of:
receiving an input indicative of a desired molecular agent;
identifying, based on the desired molecular agent, at least a first imaging system reconstruction parameter employed by a reconstruction system of the imaging system to generate an image wherein the reconstruction parameter adjusts count optimization through a dual match filter; and
communicating the imaging system reconstruction parameter to the imaging system.

27. The computer readable storage medium of claim 26, wherein the input includes patient demographic information and wherein the method includes using the demographic information to determine the desired molecular agent.

28. The computer readable storage medium of claim 26 wherein identifying includes retrieving the imaging system reconstruction parameter from a database.

29. A user interface apparatus comprising:
a computer input device which receives a user input identifying one of at least first and second molecular agents;
a computer display device which displays an identified reconstruction system protocol, which is employed by a reconstruction system of an imaging system to generate an image, based on the one of at least the first and the second molecular agents, wherein the computer display device further display information derived from an imaging examination of an object conducted using the identified molecular agent, wherein the information is displayed in human readable form according a display protocol, wherein the displayed protocol is automatically established based on the user input, and wherein the displayed protocol includes a reconstruction parameter that adjusts count optimization through a dual match filter.

30. The user interface apparatus of claim 29 wherein the first display protocol specifies a presentation of the information in a format which includes one or more image slices, three dimensional rendered views, functional parameter maps, or diagnostic annotations.

31. The user interface apparatus of claim 30 wherein the computer input device includes at least one of a scanner, an electronic communications interface, and a keyboard.

32. The user interface apparatus of claim 29 wherein the user input includes patient demographic information.

33. The user interface apparatus of claim 29 wherein the user interface is operatively connected to the imaging system and wherein the user input is used to automatically establish at least one of an acquisition, reconstruction, and detection characteristic of the imaging system.

34. The user interface apparatus of claim 29 wherein the display protocol is automatically selected from at least first and second display protocols.

35. The user interface apparatus of claim 29 wherein the user interface apparatus includes a graphical user interface.

36. A method of providing an imaging agent comprising:
defining a region of interest and an imaging modality;
selecting a molecular imaging agent which targets the region of interest and which is visible in the defined modality;
automatically establishing a reconstruction system protocol, employed by a reconstruction system of an imaging system to generate an image, based on the desired molecular agent, wherein the reconstruction system protocol includes a reconstruction parameter that adjusts count optimization through a dual match filter;
defining a set of parameters that allow for an optimization of an imaging system of the defined modality based at least on the reconstruction system protocol; and
providing the set of parameters to the imaging system.

37. The method of claim 26 wherein the set of parameters includes at least one of a, acquisition, a reconstruction, and a display parameter.

* * * * *